(12) United States Patent
Ueda et al.

(10) Patent No.: US 9,532,957 B2
(45) Date of Patent: Jan. 3, 2017

(54) METHOD OF STABILIZING REDUCED COENZYME $Q_{10}$

(71) Applicant: Kaneka Corporation, Osaka (JP)

(72) Inventors: Takahiro Ueda, Takasago (JP); Tadao Ono, Takasago (JP); Mitsutoshi Moro, Takasago (JP); Shiro Kitamura, Takasago (JP); Yasuyoshi Ueda, Takasago (JP)

(73) Assignee: KANEKA CORPORATION, Osaka (JP)

( * ) Notice: Subject to any disclaimer, the term of this patent is extended or adjusted under 35 U.S.C. 154(b) by 75 days.

(21) Appl. No.: 14/197,347

(22) Filed: Mar. 5, 2014

(65) Prior Publication Data

US 2014/0212402 A1    Jul. 31, 2014

Related U.S. Application Data

(62) Division of application No. 10/492,122, filed as application No. PCT/JP02/10515 on Oct. 10, 2002, now Pat. No. 8,703,155.

(30) Foreign Application Priority Data

Oct. 10, 2001 (JP) .................. 2001-312179
Apr. 17, 2002 (JP) .................. 2002-114879

(51) Int. Cl.

| | |
|---|---|
| A61K 31/122 | (2006.01) |
| A61K 47/10 | (2006.01) |
| A61K 47/12 | (2006.01) |
| A61K 47/14 | (2006.01) |
| A61K 47/22 | (2006.01) |
| B01D 9/00 | (2006.01) |
| C07C 41/26 | (2006.01) |
| C07C 41/40 | (2006.01) |
| C07C 41/46 | (2006.01) |
| C07C 43/23 | (2006.01) |
| A61K 9/48 | (2006.01) |

(52) U.S. Cl.
CPC ............ *A61K 31/122* (2013.01); *A61K 47/10* (2013.01); *A61K 47/12* (2013.01); *A61K 47/14* (2013.01); *A61K 47/22* (2013.01); *B01D 9/00* (2013.01); *C07C 41/26* (2013.01); *C07C 41/40* (2013.01); *C07C 41/46* (2013.01); *C07C 43/23* (2013.01); *A61K 9/4866* (2013.01)

(58) Field of Classification Search
None
See application file for complete search history.

(56) References Cited

U.S. PATENT DOCUMENTS

| | | |
|---|---|---|
| 3,066,080 A | 10/1961 | Folkers et al. |
| 3,162,657 A | 12/1964 | Crane et al. |
| 6,184,255 B1 | 2/2001 | Mae et al. |
| 6,207,137 B1 | 3/2001 | Shuch et al. |
| 6,740,338 B1 | 5/2004 | Chopra |
| 2004/0197886 A1 | 10/2004 | Ueda et al. |
| 2004/0214301 A1 | 10/2004 | Ueda et al. |
| 2004/0215040 A1 | 10/2004 | Ueda et al. |
| 2005/0070481 A1 | 3/2005 | Fujii et al. |

FOREIGN PATENT DOCUMENTS

| | | |
|---|---|---|
| CN | 1226823 A | 8/1999 |
| DE | 19806947 A1 | 8/1999 |
| GB | 947643 A | 1/1964 |

(Continued)

OTHER PUBLICATIONS

PubChem Open Chemistry Database "Citric Acid" accessed May 23, 2016, 13 pages.*
Abcam Product Datasheet "Coenzyme Q10" accessed May 23, 2016, 2 pgs.*
Caymen Chemical Product Information "Coenzyme Q10" accessed May 23, 2016, 1 pg.*
International Search Report from corresponding International Applications No. PCT/JP02/10515, dated Jan. 28, 2003, 2 pages.
Patent Cooperation Treaty International Preliminary Examination Report (PCT Article 36 and Rule 70) from corresponding International Application No. PCT/JP2002/010515, dated Nov. 28, 2003, 4 pages.

(Continued)

*Primary Examiner* — Thane Underdahl
(74) *Attorney, Agent, or Firm* — Polsinelli PC

(57) ABSTRACT

The present invention provides a stabilization method, a preservation method and the like method of reduced coenzyme $Q_{10}$, which is useful as functional nutritive foods, specific health foods and the like. Furthermore, the present invention provides a method for efficiently obtaining reduced coenzyme $Q_{10}$ of high quality and by a method suitable for a commercial production. It is possible to handle and stably preserve reduced coenzyme $Q_{10}$ under a condition that oxidation by a molecular oxygen is inhibited by contacting reduced coenzyme $Q_{10}$ with, an ascorbic acid and citric acid or a related compound thereof, and thus a stabilized composition is obtained. Moreover, reduced coenzyme $Q_{10}$ is converted into a crystalline state in such a condition that the formation of oxidized coenzyme $Q_{10}$ as a byproduct is minimized by crystallizing reduced coenzyme $Q_{10}$ in the presence of ascorbic acid or a related compound thereof etc., and thus a reduced coenzyme $Q_{10}$ crystal of high quality is produced. Furthermore, by successively crystallizing the generated reduced coenzyme $Q_{10}$ in the presence of ascorbic acid or related compound thereof after reducing oxidized coenzyme $Q_{10}$ to reduced coenzyme $Q_{10}$ using ascorbic acid or a related compound thereof, operations are simplified and minimized, and thus reduced coenzyme $Q_{10}$ of high quality is produced.

22 Claims, No Drawings

(56) References Cited

FOREIGN PATENT DOCUMENTS

| | | | |
|---|---|---|---|
| JP | 2001-064184 | A | 3/2001 |
| JP | 2003-119126 | A | 4/2003 |
| JP | 2003-119127 | A | 4/2003 |
| WO | WO-98/07417 | A1 | 2/1998 |
| WO | WO-01/52822 | A1 | 7/2001 |
| WO | WO-02/090304 | A1 | 11/2002 |

* cited by examiner

METHOD OF STABILIZING REDUCED COENZYME $Q_{10}$

CROSS REFERENCE TO RELATED APPLICATIONS

This application is a Divisional of U.S. Application No. 10/492,122 filed on Aug. 30, 2004, which is a nationalization of PCT Application No. PCT/JP02/10515 filed Oct. 10, 2002. This application claims priority from Japanese Patent Application No. 2001-312179 filed on Oct. 10, 2001 and Japanese Patent Application No. 2002-114879 filed on Apr. 17, 2002.

TECHNICAL FIELD

The present invention relates to a stabilization method of reduced coenzyme $Q_{10}$, and a preservation method, an isolation (crystallization) method and a composition of reduced coenzyme $Q_{10}$ using said stabilization method. Furthermore, it also relates to a production method of reduced coenzyme $Q_{10}$. Reduced coenzyme $Q_{10}$ shows a higher level of oral absorbability as compared with oxidized coenzyme $Q_{10}$, which has already been need as foods, etc., and it is a compound useful as an ingredient in good foods, functional nutritive foods, specific health foods, nutritional supplements, nutrients, animal drugs, drinks, feeds, cosmetics, medicines, remedies, preventive drugs, etc.

BACKGROUND ART

Oxidized coenzyme $Q_{10}$, which is a benzoquinone derivative widely distributed in the living world, is also called vitamin Q because of its vitamin-like function and is an ingredient acting as a nutrient in restoring the cell activity that has been weakened to its healthy condition and rejuvenating a living body. On the other hand, reduced coenzyme $Q_{10}$ is derived from oxidized coenzyme $Q_{10}$ by two-electron reduction. Reduced coenzyme $Q_{10}$ is a white crystal whereas oxidized coenzyme $Q_{10}$ is an orange crystal. Reduced coenzyme $Q_{10}$ and oxidized coenzyme $Q_{10}$ are known to be localized in mitochondrion, lysosome, Golgi body, microsome, peroxisome, cell membrane, etc., and involved, as constituents of the electron transport system, in ATP production and activation, antioxidant activity in a living body, and membrane stabilization. They are thus substances indispensable for maintenance of living body functions. Reduced coenzyme $Q_{10}$ is readily oxidized to oxidized coenzyme $Q_{10}$ by a molecular oxygen. Complete oxygen elimination or blocking is very difficult to be achieved in a commercial scale production, preservation or handling and, furthermore, fairly long periods of time are required for individual operations, unlike a laboratory scale production. Thus, residual oxygen exerts great adverse effects such as oxidation of reduced coenzyme $Q_{10}$ to oxidized coenzyme $Q_{10}$. As described above, it is difficult to obtain a reduced coenzyme $Q_{10}$ crystal of high quality on a commercial scale. Even if reduced coenzyme $Q_{10}$ of high quality could be produced, oxidation stability of reduced coenzyme $Q_{10}$ is a very important subject in processing them into foods, functional nutritive foods, specific health foods, nutrients, nutritional supplements, animal drugs, drinks, feeds, cosmetics, medicines, remedies, preventive drugs, etc., or into materials and compositions thereof, and/or in preserving them, after the process. Also in the process and the preservation mentioned above, complete oxygen elimination or blocking is quite difficult. Particularly in heating during the process or preservation for a long period of time, residual or immixing oxygen exerts a great adverse effect. Thus, protection against oxidation in the above-merit toned production, keeping, handling, process and preservation is very important. Oxidized coenzyme $Q_{10}$, which is a byproduct yielded by oxidation of the above reduced coenzyme $Q_{10}$, decreases a yield of reduced coenzyme $Q_{10}$. Furthermore, oxidized coenzyme $Q_{10}$ is difficult to be separated from reduced coenzyme $Q_{10}$, therefore immixes in the reduced coenzyme Oho product as an impurity and thereby decreases purity or makes the obtained crystal yellowish. Consequently, a problem that consumers or customers feel a sense of discomfort, or the like problem occurs.

It is known, that, reduced coenzyme $Q_{10}$ can be prepared by producing coenzyme $Q_{10}$ in the conventional manner, for example by synthesis, fermentation, or extraction from natural products, and concentrating a reduced coenzyme $Q_{10}$-containing eluate fraction resulting from chromatography (JP-A-10-105933). On that occasion, as described in the above-cited publication, the chromatographic concentration may be carried out after reduction of oxidized coenzyme $Q_{10}$ contained in the reduced coenzyme $Q_{10}$ as an impurity with a conventional reducing agent such as sodium, borohydride or sodium dithionite (sodium hyposulfite), or reduced coenzyme $Q_{10}$ may be prepared by reacting an existing highly pure grade of coenzyme $Q_{10}$ with the reducing agent mentioned above. Additionally, a method is also known which comprises using zinc as a reducing agent (Journal of Lavelled Compounds, vol. 6, 1970, 66-75). However, the above-mentioned methods of producing reduced coenzyme $Q_{10}$ are not necessarily satisfiable. For example, a method comprising using chromatography is complicated for a commercial scale application. And the above reducing agent has problems such as generation of gas (hydrogen, sulfur dioxide, etc,), bad smell, issue of safety, treatment difficulty after use, and handling difficulty when it is applied on a commercial scale or when producing reduced coenzyme $Q_{10}$ used for foods, functional nutritive foods, specific health foods, nutritional supplements, nutrients, animal drugs, drinks, feeds, cosmetics, medicines, remedies, preventive drugs, etc., thus is not necessarily preferable. A method for obtaining reduced coenzyme $Q_{10}$ by the above reducing agent after obtaining a fraction of coenzyme $Q_{10}$ by chromatography is not more unpreferable as a commercial production method. When the process and aftertreatment are complicated, deterioration in quality occurs as a result of the after-mentioned oxidation by a molecular oxygen.

Furthermore, in isolation of reduced coenzyme $Q_{10}$ obtained by the above-mentioned method, it is not necessarily easy to isolate it in the state of high purity due to instability of reduced coenzyme $Q_{10}$ for a molecular oxygen. In many cases, for example, the reduced coenzyme $Q_{10}$ tends to occur as a low-purity crystalline, a semisolid or an oil containing such impurities as oxidized coenzyme $Q_{10}$. As described above, it is very difficult to obtain a reduced coenzyme $Q_{10}$ crystal of high quality even If a reaction mixture of reduced coenzyme $Q_{10}$ containing completely or almost no oxidized coenzyme $Q_{10}$ could be obtained by a redaction reaction.

Thus, it is a vary important subject to stabilize reduced coenzyme $Q_{10}$, namely to protect reduced coenzyme $Q_{10}$ against oxidation. However, since reduced coenzyme $Q_{10}$ has not commercially been available so far, there has hardly been any research on a method for stably retaining reduced coenzyme $Q_{10}$ or the like method. Only WO 01/52822 A1 describes a composition containing a reducing agent and a production method thereof.

The above WO 01/52822 A1 discloses a method for producing reduced coenzyme $Q_{10}$ which comprises reduction using various reducing agents such as vitamin C (i.e. ascorbic acid or related compounds such as ascorbic acid, ascorbyl palpitate and ascorbyl stearate) and vitamin E as more preferable reducing agents which may be used for foods, etc. The specification also discloses a composition comprising reduced coenzyme $Q_{10}$, a reducing agent, and a surfactant, a vegetable oil or a mixture of these, and a composition for oral administration which is prepared in the form of a gelatin capsule or a tablet. Furthermore, the specification also discloses an in situ preparation method comprising using oxidized coenzyme $Q_{10}$ and a reducing agent as a method for obtaining said compositions.

The above composition and the preparation method thereof are complicated and cumbersome. It is presumably because the above composition is expected to have plural roles (i.e. firstly, a composition to be a reaction field where oxidized coenzyme $Q_{10}$ is reduced to reduced coenzyme $Q_{10}$, and secondly, a composition which stably retains reduced coenzyme $Q_{10}$). In other words, the above composition and the preparation method thereof makes it possible to reduce oxidized coenzyme $Q_{10}$ to reduced coenzyme $Q_{10}$ under a highly specific environment, as well as to stably retain the obtained reduced coenzyme $Q_{10}$. However, the above method comprises reduction in the presence of components having a high boiling point or fat-soluble components, such as surfactants and vegetable oils, and it is very difficult to isolate reduced coenzyme $Q_{10}$ after a reduction reaction. Therefore, applications of the above stabilization method and the composition are substantially limited to direct uses for foods, etc. The above method is an in situ preparation capable of retaining reduced coenzyme $Q_{10}$ in pure state only in a reaction mixture.

The above WO 01/52822 A1 describes that compositions disclosed therein may contain, for example, as a solvent, an organic solvent such as a polyhydric alcohol, i.e. glycerine, 1,2-propanediol (propylene glycol) or the like, and ethanol in 0.25 to 50% by weight, preferably 1 to 2-5% by weight, more preferably 1.5 to 15-20% by weight if necessary. However, the above polyhydric alcohols and ethanol are not essential components. And, among Examples in said specification. Example 2 describes a composition without containing these solvents. Example 4 describes a composition containing 1.63.%. by weight of glycerine or propylene glycol, and Examples 1 and 3 respectively describe compositions each containing 4% by weight and 3.55% by weight of glycerine.

As a result of preliminary investigations on stabilization of reduced coenzyme $Q_{10}$, the present inventors found that vitamin C has a stabilization effect whereas vitamin E does not have the effect, and a stabilization effect becomes very poor when vitamin C is used with polyhydric alcohols having 3 or more OH, such as glycerine, in combination.

In the above WO 01/52822 A1, there is no detail description on quality, stabilization effect, etc. of reduced coenzyme $Q_{10}$ contained in the composition. And also there is no disclosure that a combination of vitamin. C and a mono- and/or dihydric alcohol, especially a combination of vitamin C and a monohydric alcohol, exerts a significantly excellent stabilization effect. Furthermore, there is no description on a crystallization method, a composition, handling or preservation (including long-term stable preservation within an possible temperature range in ordinary conditions) which utilize the stabilization affect obtained by combinedly using vitamin C and a mono- and/or dihydric alcohol.

Thus, conventional methods were not necessarily satisfiable in producing reduced coenzyme $Q_{10}$ by reducing oxidized coenzyme $Q_{10}$, and in stably preserving it. Under such circumstances, it has been desired for developing a highly versatile stabilization method which overcomes the above-mentioned problems, and a preservation method, an isolation (crystallization) method and a composition using said stabilization method. Moreover, it has also been desired for developing a production method readily used for various applications by which reduced coenzyme $Q_{10}$ of high quality may be obtained not only as a reaction mixture, but also preferably as a crystal.

SUMMARY OF THE INVENTION

In view of the above-mentioned state of the art, the present invention has for its object to provide a convenient and preferable stabilization method of reduced coenzyme $Q_{10}$, and a preservation method, an isolation (crystallization) method and a composition of reduced coenzyme $Q_{10}$ using said stabilization method. Furthermore, the invention also has for its object to provide a versatile production method of reduced coenzyme $Q_{10}$ using the above stabilization method.

The present inventors concluded that if a superior stabilization method could be established, said stabilization method might be favorably used for a preservation method and/or an isolation (crystallization, production) method, or for producing a composition. Thus, as a result of intensive investigations, they found the following matters to complete the present invention.

(1) Reduced coenzyme $Q_{10}$ is preferably protected from oxidation by a molecular oxygen in the presence of citric acid or a related compound thereof and/or ascorbic acid or a related compound thereof. Particularly, it is preferably protected in the presence of a mono- or dihydric alcohol and/or a water-soluble solvent other than alcohols.

(2) Reduced coenzyme $Q_{10}$ may be converted into a crystalline state in such a condition that the formation of oxidized coenzyme $Q_{10}$ as a byproduct is minimized by crystallizing reduced coenzyme $Q_{10}$ in the presence of citric acid or a related compound thereof and/or ascorbic acid or a related compound thereof. Thereby, a reduced coenzyme $Q_{10}$ crystal of high quality may be obtained. Particularly, crystallization may be favorably carried out in the presence of a mono- or dihydric alcohol and/or a water-soluble solvent other than alcohols.

(3) Reduced coenzyme $Q_{10}$ may be converted into a crystalline state in such a condition that the formation of oxidized coenzyme $Q_{10}$ as a byproduct is minimized by reducing oxidized coenzyme $Q_{10}$ to reduced coenzyme $Q_{10}$ using ascorbic acid or a related compound thereof, and then successively crystallizing the generated reduced coenzyme $Q_{10}$ in the presence of ascorbic acid or a related compound thereof. Thereby, a reduced coenzyme $Q_{10}$ crystal of high quality may be obtained. Particularly, crystallization may be favorably carried out in the presence of ascorbic acid or a related compound thereof, and a mono- or dihydric alcohol and/or a water-soluble solvent other than alcohols.

That is, the present invention relates to a method of stabilizing reduced coenzyme $Q_{10}$ which comprises subjecting reduced coenzyme $Q_{10}$ to be coexisted with citric acid or a related compound thereof.

In addition, the present invention relates to a method of stabilizing reduced coenzyme $Q_{10}$ which comprises stabilizing reduced coenzyme $Q_{10}$ by coexistence of reduced coenzyme $Q_{10}$ and ascorbic acid or a related compound thereof, said coexistence being carried out in the presence of a mono- or dihydric alcohol and/or a water-soluble solvent other than alcohols, and content of said mono- or dihydric alcohol and/or the water-soluble solvent other then alcohols being 5% by weight or snore in a whole mixture.

Moreover, the present invention relates to a method of crystallizing reduced coenzyme $Q_{10}$ which comprises crystallizing reduced coenzyme $Q_{10}$ in a solvent containing citric acid or a related compound thereof and/or ascorbic acid or a related compound thereof.

Furthermore, the present invention relates to a method of producing reduced coenzyme $Q_{10}$ crystal which comprises reducing oxidized coenzyme $Q_{10}$ to reduced coenzyme $Q_{10}$ using ascorbic acid or a related compound thereof, and successively crystallizing the generated reduced coenzyme $Q_{10}$ in the presence of citric acid or a related compound thereof and/or ascorbic acid or a related compound thereof.

And the present invention also relates to a method of preserving reduced coenzyme $Q_{10}$ which comprises preserving reduced coenzyme $Q_{10}$ stabilized by said method in a preservation condition of 50° C. or below.

The present invention further relates to a composition containing reduced coenzyme $Q_{10}$ which comprises reduced coenzyme $Q_{10}$ and citric acid or a related compound thereof.

Additionally, the present invention also relates to a composition containing reduced coenzyme $Q_{10}$ which comprises reduced coenzyme $Q_{10}$, ascorbic acid or a related compound thereof, and a mono- or dihydric alcohol and/or a water-soluble solvent other than alcohols, and content of said mono- or dihydric alcohol and/or the water-soluble solvent other than alcohols being 5% by weight or more in a whole composition, In the present invention, an agent which is safe and easy to handle may be used, and a solvent to be used may be suitably selected according to the purpose and application. Furthermore, the present invention is also suitably utilizable for isolation or further derivatization of reduced coenzyme $Q_{10}$, and for compositions for foods, medical purpose and the like, thus has a great advantage.

DETAILED DESCRIPTION OF THE INVENTION

Hereinafter, the present invention is described in detail.

In practice of the present invention, citric acid or a related compound thereof and/or ascorbic acid or a related compound thereof are used to stabilize reduced coenzyme $Q_{10}$ while controlling oxidation of reduced coenzyme $Q_{10}$ to oxidized coenzyme $Q_{10}$, or to stably preserve reduced coenzyme $Q_{10}$, and further to obtain a reduced coenzyme $Q_{10}$ crystal of high quality.

The citric acid or a related compound thereof is not particularly restricted, and there may be mentioned citric acid, citrates such as isopropyl citrate, ethyl citrate. butyl citrate, glyceride citrate and the like, and further salts such as sodium citrate, potassium citrate and the like. Particularly preferred are citric acid, isopropyl citrate and glyceride citrate. In the stabilization method, preservation method, crystallization method and the composition of reduced coenzyme $Q_{10}$ according to the present invention, the above-mentioned citric acid or a related compound thereof may be freely selected according to the purpose and application. These citric acid or a related compound thereof may be used singly or in combination. It is also allowable to use them in combination with ascorbic acid or a related compound thereof described below.

The ascorbic acid or a related compound thereof is not particularly restricted, and include, for example, not only ascorbic acid, but also rhamno-ascorbic acid, arabo-ascorbic acid, gluco-ascorbic acid, fuco-ascorbic acid, glucohepto-ascorbic acid, xylo-ascorbic acid, galacto-ascorbic acid, gulo-ascorbic acid, allo-ascorbic acid, erythro-ascorbic acid, 6-desoxyascorbic acid, and the like ascorbic acid derivatives, and may be esters or salts of these. These may be L-form, D-form or racemic form. More specifically, there may be mentioned, for example, L-ascorbic acid, L-ascorbyl palmitate, L-ascorbyl stearate, L-ascorbyl 2 palmitate, L-sodium ascorbate, L-calcium ascorbate, D-arabo-ascorbic acid, etc. In producing a reduced coenzyme $Q_{10}$ crystal of the present invention, any of the above-mentioned ascorbic acid and a related compound thereof may be preferably used. However, ones which are highly water-soluble are preferably used in particular among the above-mentioned ascorbic acid or a related compound thereof in view of separation from the generated reduced coenzyme $Q_{10}$ or the like. And most preferred is a free form one such as L-ascorbic acid, D-arabo-ascorbic acid and the like in view of the ready availability, price or the like. In the stabilization method, preservation method, crystallization method and the composition of reduced coenzyme $Q_{10}$ according to the present invention, the above-mentioned ascorbic acid or a related compound thereof may be freely selected according to the purpose and application. The ascorbic acid or a related compound thereof may be used singly or in combination. It is also allowable to use them in combination with the above-mentioned citric acid or a related compound thereof.

The above-mentioned citric acid or a related compound thereof and/or ascorbic acid or a related compound thereof may be used in any of the stabilization method, preservation method, crystallization method and the composition of reduced coenzyme $Q_{10}$ according to the present invention. Additionally, in the production method of a reduced coenzyme $Q_{10}$ crystal according to the present invention, the above ascorbic acid or a related compound thereof is particularly preferably used. According to need, the citric acid or a related compound thereof may be used in combination.

A form of reduced coenzyme $Q_{10}$ to coexist with citric acid or a related compound thereof and/or ascorbic acid or a related compound thereof, that is, a form of reduced coenzyme $Q_{10}$ on contacting with citric acid or a related compound thereof and/or ascorbic acid or a related compound thereof is not particularly restricted. For example, there may be mentioned a form in which both reduced coenzyme $Q_{10}$ and citric acid or a related compound thereof and/or ascorbic acid or a related compound thereof exist as solid phases, a form in which at least one of citric acid or a related compound thereof and/or ascorbic acid or a related compound thereof exists as a solid phase in a reduced coenzyme $Q_{10}$-containing liquid phase, a form in which reduced coenzyme $Q_{10}$ exists as a solid phase in a liquid phase containing at least one of a citric acid or a related compound thereof and/or an ascorbic acid or a related compound thereof, a form in which both reduced coenzyme $Q_{10}$ and citric acid or a related compound thereof and/or ascorbic acid or a related compound thereof are liquid phases or exist in a liquid phase, etc. The above-mentioned liquid phase may be either homogeneous or inhomogeneous (consisting of multiple different liquid phases), but is preferably homogeneous. Needless to say, a system, whose contact efficiency of reduced coenzyme $Q_{10}$ with citric acid or a related compound thereof and/or ascorbic acid or a related compound thereof is higher, is preferred for oxidation protection. Particularly preferred is the form in which both reduced coenzyme $Q_{10}$ and citric acid or a related compound thereof and/or ascorbic acid or a related compound thereof are liquid phases or exist in a liquid phase, and the liquid phase is preferably homogeneous. Needless to say, the reduced coenzyme $Q_{10}$-containing liquid phase may be a reduced coenzyme $Q_{10}$ solution, or may be a reduced coenzyme $Q_{10}$ melt.

Solvents which may be used in the present invention are not particularly restricted, and there may be mentioned hydrocarbons, fatty acid esters, ethers, alcohols, fatty acids, ketones, nitrogen compounds (including nitriles and amides), sulfur-containing compounds, water, etc. These solvents may also be used as a mixture comprising any two or more species.

The hydrocarbons are not particularly restricted, but there may be mentioned, for example, aliphatic hydrocarbons, aromatic hydrocarbons, halogenated hydrocarbons, etc. Among them, preferred are aliphatic hydrocarbons and aromatic hydrocarbons, and particularly preferred are aliphatic hydrocarbons.

The aliphatic hydrocarbons are not particularly restricted, and may be cyclic or acyclic, and saturated or unsaturated. Generally, however, saturated ones are preferably used. Usually, they contain preferably 3 to 20 carbon atoms, more preferably 5 to 12 carbon atoms, and still more preferably 5 to 8 carbon atoms. As specific examples, there may be mentioned, for example, propane, butane, isobutane, pentane, 2-methylbutane, hexane, 2-methylpentane, 2,2-dimethylbutane, 2,3-dimethylbutane, heptane, heptane isomers (e.g. 2-methylhexane, 3-methylhexane, 2,3-dimethylpentane, 2,4-dimethylpentane), octane, 2,2,3-trimethylpentane, isooctane, nonane, 2,2,5-trimethylhexane, decane, dodecane, 2-pentene, 1-hexene, 1-heptene, 1-octene, 1-nonene, 1-decene, cyclopentane, methylcyclopentane, cyclohexane, methylcyclohexane, ethylcyclohexane, p-menthane, cyclohexane, etc. Preferred are pentane, 2-methylbutane, hexane, 2-methylpentane, 2,2-dimethylbutane, 2,3-dimethylbutane, heptane, heptane isomers (e.g. 2-methylhexane, 3-methylhexane, 2,3-dimethylpentane, 2,4-dimethylpentane), octane, 2,2,3-trimethylpentane, isooctane, nonane, 2,2,5-trimethylhexane, decane, dodecane, cyclopentane, methylcyclopentane, cyclohexane, methylcyclohexane, ethylcyclohexane, p-menthane, etc. Particularly preferred are pentane, 2-methylbutane, hexane, 2-methylpentane, 2,2-dimethylbutane, 2,3-dimethylbutane, heptane, heptane isomers (e.g. 2-methylhexane, 3-methylhexane, 2,3-dimethylpentane, 2,4-dimethylpentane), octane, 2,2,3-trimethylpentane, isooctane, cyclopentane, methylcyclopentane, cyclohexane, methylcyclohexane, ethylcyclohexane, etc. Generally, preferably used are heptanes, which include heptane isomers such as methylcyclohexane having 7 carbon atoms as well as heptane, and a plural mixture thereof, usually, preferred are pentanes having 5 carbon atoms (e.g. pentane, etc.), hexanes having 6 carbon atoms (e.g. hexane, cyclohexane, etc.), heptanes having 7 carbon atoms (e.g. heptane, methylcyclohexane, etc.) and the like. Most preferred are heptanes (e.g. heptane, methylcyclohexane, etc.), and among them, heptane is particularly preferred.

The aromatic hydrocarbons are not particularly restricted, generally, however, they contain 6 to 20 carbon atoms, preferably 6 to 12 carbon atoms, and more preferably 7 to 10 carbon atoms. As specific examples, there may be mentioned, for example, benzene, toluene, xylene, o-xylene, m-xylene, p-xylene, ethylbenzene, cumene, mesitylene, tetralin, butylbenzene, p-cymene, cyclohexylbenzene, diethylbenzene, pentylbenzene, dipentylbenzene, dodecylbenzene, styrene, etc. Preferred are toluene, xylene, o-xylene, m-xylene, p-xylene, ethylbenzene, cumene, mesitylene, tetralin, butylbenzene, p-cymene, cyclohexylbenzene, diethylbenzene, pentylbenzene, etc. Particularly preferred are toluene, xylene, o-xylene, m-xylene, p-xylene, cumene, tetralin, etc. and most preferred is cumene.

The halogenated hydrocarbons are not particularly restricted, and may be cyclic or acyclic, and saturated or unsaturated. Generally, however, acyclic ones are preferably used. Usually, preferred are chlorinated hydrocarbons and fluorinated hydrocarbons, and chlorinated hydrocarbons are particularly preferred. Preferably used are ones containing 1 to 6 carbon atoms, more preferably used are ones containing 1 to 4 carbon atoms, and still more preferably used are ones containing 1 to 2 carbon atoms. As specific examples, for example, there may be mentioned dichloromethane, chloroform, carbon tetrachloride, 1,1-dichloroethane, 1,2-dichloroethane, 1,1,1-trichloroethane, 1,1,2-trichloroethane, 1,1,1,2-tetrachloroethane, 1,1,2,2-tetrachloroethane, pentachloroethane, hexachloroethane, 1,1-dichloroethylene, 1,2-dichloroethylene, trichloroethylene, tetrachloroethylene, 1,2-dichloropropane, 1,2,3-trichloropropane, chlorobenzene, 1,1,1,2-tetrafluoroethane, etc. Preferred are dichloromethane, chloroform, carbon tetrachloride, 1,1-dichloroethane, 1,2-dichloroethane, 1,1,1-trichloroethane, 1,1,2-trichloroethane, 1,1-dichloroethylene, 1,2-dichloroethylene, trichloroethylene, chlorobenzene, 1,1,1,2-tetrafluoroethane, etc. Particularly preferred are dichloromethane, chloroform, 1,2-dichloroethylene, trichloroethylene, chlorobenzene, 1,1,1,2-tetrafluoroethane, etc.

The fatty acid esters are not particularly restricted, but there may be mentioned, for example, propionates, acetates, formates, etc. Among them, preferred are acetates and formates, and particularly preferred are acetates. Ester functional groups thereof are not particularly restricted, but there may be mentioned alkyl esters or aralkyl asters having 1 to 8 carbon atoms, etc. Preferred are alkyl esters having 1 to 6 carbon atoms, and more preferred are alkyl esters having 1 to 4 carbon atoms. As specific examples of the propionates, there may be mentioned, for example, methyl propionate, ethyl propionate, butyl propionate, isopentyl propionate, etc. As specific examples of the acetates, there may be mentioned, for example, methyl acetate, ethyl acetate, propyl acetate, isopropyl acetate, butyl acetate, isobutyl acetate, sec-butyl acetate, pentyl acetate, isopentyl acetate, sec-hexyl acetate, cyclohexyl acetate, benzyl acetate, etc. Preferred are methyl acetate, ethyl acetate, propyl acetate, isopropyl acetate, butyl acetate, isobutyl acetate, sec-butyl acetate, pentyl acetate, isopentyl acetate, sec-hexyl acetate, cyclohexyl acetate, etc. Most preferred are methyl acetate, ethyl acetate, propyl acetate, isopropyl acetate, butyl acetate, isobutyl acetate, etc. Among them, particularly preferred is ethyl acetate. As specific examples of the formates, there may be mentioned, for example, methyl formate, ethyl formate, propyl formate, isopropyl formats, butyl formate, isobutyl formate, sec-butyl formate, pentyl formate, etc. Preferred are methyl formate, ethyl formate, propyl formate, butyl formate, isobutyl formate, pentyl formate, etc. and most preferred is ethyl formate.

The ethers are not particularly restricted, and may be cyclic or acyclic, and saturated or unsaturated. Generally, however, saturated ones are preferably used. Usually, preferably used are ones containing 3 to 20 carbon atoms, store preferably used are ones containing 4 to 12 carbon atoms and still more preferably used are ones containing 4 to 8 carbon atoms. As specific examples, there may be mentioned, for example, diethyl ether, methyl tert-butyl ether, dipropyl ether, diisopropyl ether, dibutyl ether, dihexyl ether, ethyl vinyl ether, butyl vinyl ether, anisol, phenetole, butyl phenyl ether, methoxytoluene, dioxane, furan, 2-methylfuran, tetrahydrofuran, tetrahydropyran, ethylene glycol dimethyl ether, ethylene glycol diethyl ether, ethylene glycol dibutyl ether, ethylene glycol monomethyl ether, ethylene glycol monomethyl ether, ethylene glycol dibutyl ether, etc. Preferred are diethyl ether, methyl tert-butyl ether, dipropyl ether, diisopropyl ether, dibutyl ether, dihexyl ether, anisol, phenetole, butyl phenyl ether, methoxytoluene, dioxane, 2-methylfuran, tetrahydrofuran, tetrahydropyran, ethylene glycol dimethyl ether, ethylene glycol diethyl ether, ethylene glycol dibutyl ether, ethylene glycol monomethyl ether, ethylene glycol monomethyl ether, etc. Particularly preferred are diethyl ether, methyl tert-butyl ether, anisol, dioxane, tetrahydrofuran, ethylene glycol monomethyl ether, ethylene glycol monomethyl ether, etc. Most preferred are diethyl ether, methyl tert-butyl ether, anisol, dioxane, tetrahydrofuran, etc., and among them, particularly preferred are dioxane and tetrahydrofuran.

The nitriles are not particularly restricted, and may be cyclic or acyclic, and saturated or unsaturated. Generally, however, saturated ones are preferably used. Usually, preferably used are ones containing 2 to 20 carbon atoms, more preferably used are ones containing 2 to 12 carbon atoms, and still more preferably used are ones containing 2 to 8 carbon atoms.

As specific examples, there may be mentioned, for example, acetonitrile, propiononitrile, malononitrile, butyronitrile, isobutyronitrile, succinonitrile, valeronitrile, glutaronitrile, hexanenitrile, heptylcyanide, octylcyanide, undecanenitrile, dodecanenitrile, tridecanenitrile, pentadecanenitrile, stearonitrile, chloroacetonitrile, bromoacetonitrile, chloropropiononitrile, bromopropiononitrile, methoxyacetonitrile, methyl cyanoacetate, ethyl cyanoacetate, tolunitrile, benaonitrile, chlorobenzonitrile, bromobenzonitrile, cyanobenzoic acid, nitrobenzonitrile, anisonitrile, phthalonitrile, bromotolunitrile, methyl cyanobenzoate, methoxybenzonitrile, acetylbenzonitrile, naphthonitrile, biphenylcarbonitrile, phenylpropiononitrile, phenylbutyronitrile, methylphenylacetonitrile, diphenylacetonitrile, naphthylacetonitrile, nitrophenylacetonitrile, chlorobenzylcyanide, cyclopropanecarbonitrile, cyclohexanecarbonitrile, cycloheptanecarbonitrile, phenylcyclohexanecarbonitrile, tolylcyclohexanecarbonitrile, etc. Among them, acetonitrile is preferred.

The alcohols are not particularly restricted but may be cyclic or acyclic, and saturated or unsaturated. Generally, however, saturated ones are preferably used. Usually, preferred are monohydric alcohols containing 1 to 20 carbon atoms, more preferred are those containing 1 to 12 carbon atoms, still more preferred are those containing 1 to 6 carbon atoms, and particularly preferred are those containing 1 to 5 carbon atoms. Dihydric alcohols containing 2 to 5 carbon atoms are also preferred. As specific examples of these alcohols, there may be mentioned, for example, methanol, ethanol, 1-propanol, 2-propanol, 1-butanol, 2-butanol, isobutyl alcohol, tert-butyl alcohol, 1-pentanol, 2-pentanol, 1-pentanol, 2-methyl-1-butanol, isopentyl alcohol, tert-pentyl alcohol, 3-methyl-2-butanol, neopentyl alcohol, 1-hexanol, 2-methyl-1-pentanol, 4-methyl-2-pentanol, 2-ethyl-1-butanol, 1-heptanol, 2-heptanol, 3-heptanol, 1-octanol, 2-octanol, 2-ethyl-1-hexanol, 1-nonanol, 1-decanol, 1-undecanol, 1-dodecanol, allyl alcohol, propargyl alcohol, benzyl alcohol, cyclohexanol, 1-methylcyclohexanol, 2-methylcyclohexanol, 3-methylcyclohexanol, 4-methylcyclohexanol, 2-methoxyethanol, 2-ethoxyethanol, 2-(methoxymethoxy)ethanol, 2-isopropoxyethanol, 2-butoxyethanol, 2-(isopentyloxy)ethanol, 2-(hexloxy)ethanol, furfuryl alcohol, diethylene glycol monomethyl ether, diethylene glycol monomethyl ether, diethylene glycol monobuthyl ether, triethylene glycol monomethyl ether, 1-methoxy-2-propanol, 1-ethoxy-2-propanol, dipropyleneglycol monomethyl ether, dipropylene glycol monomethyl ether, tripropyleneglycol monomethyl ether, 1,2-ethanediol, 1,2-propanediol, 1,3-propanediol, 1,2-butanediol, 1,3-butanediol, 1,4-butanediol, 2,3-butanediol, 1,5-pentanediol, 2-butene-1,4-diol, 2-methyl-2,4-pentanediol, 2-ethyl-1,3-hexanediol, diethylene glycol, triethylene glycol, tetraethylene glycol, polyethylene glycol, dipropylene glycol, polypropylene glycol, etc.

As the monohydric alcohols, preferred are methanol, ethanol, 1-propanol, 2-propanol, 1-butanol, 2-butanol, isobutyl alcohol, tert-butyl alcohol, 1-pentanol, 2-pentanol, 3-pentanol, 2-methyl-1-butanol, isopentyl alcohol, tert-pentyl alcohol, 3-methyl-2-butanol, neopentyl alcohol, 1-hexanol, 2-methyl-1-pentanol, 4-methyl-2-pentanol, 2-ethyl-1-butanol, 1-heptanol, 2-heptanol, 3-heptanol, 1-octanol, 2-octanol, 2-ethyl-1-hexanol, 1-nonanol, 1-decanol, 1-undecanol, 1-dodecanol, benzylalcohol, cyclohexanol, 1-methylcyclohexanol, 1,2-methylcyclohexanol, 3-methylcyclohexanol, 4-methylcyclohexanol, 2-methyloxyethanol, 2-ethoxyethanol, 2-(methoxymethoxy)ethanol, etc. Particularly preferred are methanol, ethanol, 1-propanol, 2-propanol, 1-butanol, 2-butanol, isobutyl alcohol, tert-butyl alcohol, 1-pentanol, 2-pentanol, 3-pentanol, 2-methyl-1-butanol, isopentyl alcohol, tert-pentyl alcohol, 3-methyl-2-butanol, neopentyl alcohol, 1-hexanol, 2-methyl-1-pentanol, 4-methyl-2-pentanol, 2-ethyl-1-butanol, cyclohexanol, etc. Among them, methanol, ethanol, 1-propanol, 2-propanol, 1-butanol, 2-butanol, isobutyl alcohol, tert-butyl alcohol, 1-pentanol, 2-pentanol, 3-pentanol, 2-methyl-1-butanol, isopentyl alcohol, tert-pentyl alcohol, 3-methyl-2-butanol, neopentyl alcohol, etc. are preferred. Most preferred are methanol, ethanol, 1-propanol, 2-propanol, 1-butanol, 2-butanol, isobutyl alcohol, 2-methyl-1-butanol, isopentyl alcohol, etc. Among them, methanol, ethanol, 1-propanol and 2-propanol are preferred, and ethanol is particularly preferred.

As the dihydric alcohols, preferred are 1,2-ethanediol, 1,2-propanediol, 1,3-propanediol, 2-butene-1,4-diol, 2-methyl-2,4-pentanediol, 2-ethyl-1,3-hexanediol, diethylene glycol, triethyiene glycol, tetraethylene glycol, polyethylene glycol, dipropylene glycol, polypropylene glycol, etc. Most preferred are 1,2-propanediol and polyethylene glycol.

When citric acid or a related compound thereof is used, trihydric alcohols may also be preferably used. As the trihydric alcohol, glycerin is preferred.

As the fatty acids, there may be mentioned, for example, formic acid, acetic acid, propionic acid, oleic acid, linoleic acid, linolenic acid, etc. Preferred are formic acid and acetic acid, and most preferred is acetic acid.

The ketones are not particularly restricted, and generally, ones having 3 to 5 carbon atoms are preferably used. As specific examples, there may be mentioned, for example, acetone, methyl ethyl ketone, methyl butyl ketone, methyl isobutyl ketone, etc. Particularly preferred are acetone and methyl ethyl, ketone, and most preferred is acetone.

As the nitrogen compounds, there may be mentioned, for example, nitromethane, triethylamine, pyridine, formamide, N-methylformamide, N,N-dimethylacetoamide, N,N-dimethylacetoamide, N-methylpyrrolidone, etc.

As the sulfur compounds, there may be mentioned, for example, dimethyl sulfoxide, sulfolane, etc.

Among the above-mentioned solvents, hydrocarbons, fatty acid esters, ethers or nitriles, and preferably water-soluble ethers or nitriles (e.g. tetrahydrofuran, dioxane, acetonitrile, etc.) have high protection effect from, oxidation. Thus, such solvents promote the stabilization effect of citric acid or a related compound thereof and/or ascorbic acid or a related compound thereof on reduced coenzyme $Q_{10}$, and are capable of inhibiting sub-generation of oxidized coenzyme $Q_{10}$.

Additionally, among the above-mentioned solvents, mono- or di-hydric alcohols and/or water-soluble solvents other than alcohols (preferably water-soluble organic solvents) make an oxidation protection effect of ascorbic acid and/or citric acid, or a related compound thereof remarkable, thus maximize the effect of the present invention. When ascorbic acid or a related, compound thereof is used, coexistence with a mono- or dihydric alcohol and/or a water-soluble solvent other than alcohols (preferably a water-soluble organic solvent) is effective, and coexistence with a monohydric alcohol is particularly effective.

As the mono- or dihydric alcohol, specifically, there may be mentioned methanol, ethanol, 1-propanol, 2-propanol, 1-butanol, 2-butanol, isobutyl alcohol, tert-butyl alcohol, 1-pentanol, 2-pentanol, 3-pentanol, 2-methyl-1-butanol, isopentyl alcohol, tert-pentyl alcohol, 3-methyl-2-butanol, neopentyl alcohol, 1-hexanol, 2-methyl-1-pentanol, 4-methyl-2-pentanol, 2-ethyl-1-butanol, 1-heptanol, 2-heptanol, 3-heptanol, 1-octanol, 2-octanol, 2-ethyl-1-hexanol, 1-nonanol, 3,5,5-trimethyl-1-hexanol, 1-decanol, 1-undecanol, 1-dodecanol, allyl alcohol, propargyl alcohol, benzyl alcohol, cyclohexanol, 1-methyl cyclohexanol, 2-methyl cyclohexanol, 3-methyl cyclohexanol, 4-methyl cyclohexanol, benzyl alcohol, 2-methoxy ethanol, 2-ethoxy ethanol, 2-(methoxymethoxy)ethanol, 2-isopropoxyethanol, 2-butoxy ethanol, 2-(isopentyloxy)ethanol, 2-(hexyloxy)ethanol, furfuryl alcohol, diethylene glycol monomethyl ether, diethylene glycol monomethyl ether, diethylene glycol monobutyl ether, triethylene glycol monomethyl ether, 1-methoxy-2-propanol, 1-ethyoxy-2-propanol, dipropylene glycol monomethyl ether, dipropylene glycol monomethyl ether, tripropylene glycol monomethyl ether, 1,2-ethanediol, 1,2-propanediol, 1,3-propanediol, 1,2-butanediol, 1,3-butanediol, 1,4-butanediol, 2,3-butanediol, 1,5-pentanediol, 2-butene-1,4-diol, 2-methyl-2,4-pentanediol, 2-ethyl-1,3-hexanediol, diethylene glycol, triethylene glycol, tetraethylene glycol, polyethylene glycol, dipropylene glycol, polypropylene glycol, etc. As the monohydric alcohol, preferred as methanol, ethanol, 1-propanol, 2-propanol, 1-butanol, 2-butanol, isobutyl alcohol, tert-butyl alcohol, 1-pentanol, 2-pentanol, 3-pentanol, 2-methyl-1-butanol, isopentyl alcohol, tert-pentyl alcohol, 3-methyl-2-butanol, neopentyl alcohol, 1-hexanol, 2-methyl-1-pentanol, 4-methyl-2-pentanol, 2-ethyl-1-butanol, 1-heptanol, 2-heptanol, 3-heptanol, 1-octanol, 2-octanol, 2-ethyl-1-hexanol, 1-nonanol, 1-decanol, 1-undecanol, 1-dodecanol, benzyl alcohol, cyclohexanol, 1-methyl cyclohexanol, 2-methyl cyclohexanol, 3-methyl cyclohexanol, 4-methyl cyclohexanol, 2-methoxy ethanol, 2-ethoxy ethanol, 2-(methoxymethoxy) ethanol, etc. More preferred are methanol, ethanol, 1-propanol, 2-propanol, 1-butanol, 2-butanol, isobutyl alcohol, tert-butyl alcohol, 1-pentanol, 2-pentanol, 3-pentanol, 2-methyl-1-butanol, isopentyl alcohol, tert-pentyl alcohol, 3-methyl-2-butanol, neopentyl alcohol, 1-hexanol, 2-methyl-1-pentanol, 4-methyl-2-pentanol, 2-ethyl-1-butanol, cyclohexanol, etc. Among them, methanol, ethanol, 1-propanol, 2-propanol, 1-butanol, 2-butanol, isobutyl alcohol, tert-butyl alcohol, 1-pentanol, 2-pentanol, 3-pentanol, 2-methyl-1-butanol, isopentyl alcohol, tert-pentyl alcohol, 3-methyl-2-butanol, neopentyl alcohol, etc. are preferred. More preferred are methanol, ethanol, 1-propanol, 2-propanol, 1-butanol, 2-butanol, isobutyl alcohol, 2-methyl-1-butanol, isopentyl alcohol, etc. Particularly preferred are methanol, ethanol, 1-propanol and 2-propanol, and most preferred is ethanol. As the dihydric alcohol, preferred are 1,2-ethanediol, 1,2-propanediol, 1,3-propanediol, 2-butene-1,4-diol, 2-methyl-2,4-pentanediol, 2-ethyl-1,3-hexanediol, diethylene glycol, triethylene glycol, tetraethylene glycol, polyethylene glycol, dipropylene glycol, polypropylene glycol, etc., and most preferred are 1,2-propanediol and polyethylene glycol.

As the water-soluble solvent other than alcohols, there may be mentioned, for example, ethers such as tetrahydrofuran and dioxane, ketones such as acetone and methyl ethyl ketone, nitrogen compounds such as acetonitrile and dimethylformamide, water, etc. Preferred are tetrahydrofuran and acetone, and more preferred is acetone.

Among them, ethanol, 1,2-propanediol, polyethylene glycol (preferably polyethylene glycol having the molecular weight of 300 to 1000), etc. are particularly preferred to be used for foods, medicinal purpose, etc. Needless to say, a mixture thereof may be preferably used.

The amount of the solvents mentioned above to be used is not particularly restricted and may be such that favorable effects or capabilities to be expected can be exerted (i.e. effective amount). For example, it is generally 5% by weight or more, preferably 10% by weight or more, more preferably 20% by weight or more, still more preferably 30% by weight or more, further more preferably 40% by weight or more, particularly preferably 50% by weight or more, and most preferably more than 50% by weight in a whole mixture.

Particularly, when ascorbic acid or a related compound thereof is used, the amount of the above solvent to be used is preferably 60% by weight or more, more preferably 70% by weight or more, and still more preferably 80% by weight or more.

Moreover, in view of maximizing the effect of citric acid or a related compound thereof and/or ascorbic acid or a related compound thereof, the solvent preferably has a simple composition, and contains substantially no vegetable oils and/or surfactants.

Firstly, the stabilization method and the preservation method of reduced coenzyme $Q_{10}$ are described.

The amount of the citric acid or a related compound thereof and/or the ascorbic acid or a related compound thereof to be used in the present invention may be, for example, such that favorable effects or capabilities to be expected can be exerted (i.e. effective amount). Specifically, it may be such an effective amount, that oxidation of reduced coenzyme $Q_{10}$ to oxidized coenzyme $Q_{10}$ can be prevented. Accordingly, although it may vary depending on the species of citric acid or a related compound thereof and/or ascorbic acid or a related compound thereof, and is not particularly restricted, the amount to be used is generally 0.1 parts by weight or more, preferably 1 part by weight or more, and more preferably 10 parts by weight or more relative to 100 parts by weight of reduced coenzymes $Q_{10}$. When a solvent is mixed, citric acid or a related compound thereof and/or ascorbic acid or a related compound thereof is generally used in an amount of 0.01 parts by weight or more, preferably 0.1 parts by weight or more, and more preferably 1 part by weight or more relative to 100 parts by weight of a solvent, although it may vary depending on the species of them.

The oxidation protection effect on reduced coenzyme $Q_{10}$ in a solvent tends to be further increased in a highly concentrated reduced coenzyme $Q_{10}$ solution. Therefore, although there is no particular restriction, it would be more effective to handle or preserve reduced coenzyme $Q_{10}$ in a solution containing generally 1 part by weight or more, and preferably 2 parts by weight or more of reduced coenzyme $Q_{10}$ relative to 100 parts by weight of a solvent.

The temperature is not particularly restricted in carrying out the stabilization method of the present invention. However, for maximizing the stabilization effect, it is generally 50° C. or less, preferably 40° C. or less, and more preferably 30° C. or less.

Therefore, an embodiment comprising preserving reduced coenzyme $Q_{10}$ stabilized by the above-mentioned stabilization method at 50° C. or less, preferably 40° C. or less, and more preferably 30° C. or less is included in the present invention.

As mentioned above, according to the present invention, it is possible to suitably protect reduced coenzyme $Q_{10}$ from oxidation by a molecular oxygen and stabilize the same by using the above-mentioned citric acid or a related compound thereof and/or ascorbic acid or a related compound thereof. Therefore, operations such as extraction, washing with water, concentration and column chromatography may be preferably carried out, and further reduced coenzyme $Q_{10}$ may be stably preserved.

Next, the crystallization method of the present invention is described. In the present invention, reduced coenzyme $Q_{10}$ is crystallized in a solvent containing citric acid or a related compound thereof and/or ascorbic acid or a related compound thereof.

The reduced coenzyme $Q_{10}$ to be subjected to crystallization can be obtained in the conventional manner, for example, by synthesis, fermentation, extraction from a natural source, etc. Preferred is reduced coenzyme $Q_{10}$ obtained by reduction of oxidized coenzyme $Q_{10}$ or the same contained in a reduced coenzyme $Q_{10}$. More preferred is reduced coenzyme $Q_{10}$ obtained by carrying out a reduction reaction in accordance with the present invention, as described below.

While the method of crystallization according to the invention can be applied also to a reduced coenzyme $Q_{10}$ product containing relatively large amounts of oxidized coenzyme $Q_{10}$, the method is particularly effective in crystallizing high-purity reduced coenzyme $Q_{10}$ prepared by the reduction method described below or the like method. In the practice of the invention, it is very effective to purify and crystallize reduced coenzyme $Q_{10}$ with simultaneous removal of impurities contained in the reduced coenzyme $Q_{10}$-containing reaction mixture or extract obtained in the conventional manner or produced by the below-mentioned reduction method or the like method. This makes it possible to remove coexisting impurities, in particular analogous compounds having similar structures and generally not always easy to be removed (specifically, reduced coenzyme $Q_9$, reduced coenzyme $Q_8$, reduced coenzyme $Q_7$, etc.) into a mother liquor. Needless to say, it is possible to utilize the above-mentioned purification and crystallization method as a recrystallization method for repurifying reduced coenzyme $Q_{10}$ crystal.

The crystallization of reduced coenzyme $Q_{10}$ may be carried out by using one of general crystallization operations such as cooling, concentration, solvent substitution and use of poor solvent etc., or by appropriately combining these operations. Using the cooling operation (cooling crystallization) singly or in combination is particularly preferred.

The amount of the citric acid or a related compound thereof and/or the ascorbic acid or a related compound thereof in the present invention to be used may be such an amount that favorable effects or capabilities to be expected can be exerted (i.e. effective amount). Specifically, it may be such an effective amount that oxidation of reduced coenzyme $Q_{10}$ to oxidized coenzyme $Q_{10}$ can be prevented. Although the amount of citric acid or a related compound thereof and/or ascorbic acid or a related compound thereof to be used may vary depending on the species and is not particularly restricted, it is generally 0.1 parts by weight or more, preferably 1 part by weight or more, and more preferably 10 parts by weight, or more relative to 100 parts by weight of reduced coenzymes $Q_{10}$, and generally 0.01 parts by weight or more, preferably 0.1 parts by weight or more relative to 100 parts by weight of a solvent. The upper limit of the amount is not particularly restricted, but also from an economical viewpoint, it may be generally 10 parts by weight or less, preferably 5 parts by weight or less, and more preferably 1 part by weight or less.

The crystallization of reduced coenzyme $Q_{10}$ is favorably carried out under forced flowing. For preventing occurrence of supersaturation and thereby allowing the nucleation and crystal growth to proceed smoothly, or in view of obtaining products of high quality, the flowing is generally brought about by stirring power consumption per unit volume of generally not less than about 0.01 kW/m$^3$, preferably not less than about 0.1 kW/m$^3$, and more preferably not less than about 0.3 kW/m$^3$. The forced flowing is generally provided by the turning of a stirring blade(s). However, the use of a stirring blade(s) is not always necessary if the above flowing can be otherwise obtained. For example, a method based on liquid circulation may be utilized.

In carrying out crystallization., a seed crystal is preferably added for preventing occurrence of supersaturation and allowing the nucleation and crystal growth proceed smoothly.

Since the crystallization temperature (cooling temperature in the step of crystallization) of reduced coenzyme $Q_{10}$ may vary depending on the species of a crystallization solvent or crystallization method, it cannot be absolutely specified. For example, however, it is preferably 25° C. or less, more preferably 20° C. or less, still more preferably 15° C. or less, and most preferably 10° C. or less. The lower limit of the temperature is the solidification temperature of a system. Thus, crystallization can be generally favorably carried out at about 0 to 25° C.

In the process of crystallization, the amount of crystals obtained per unit time may be controlled in order to minimize the contamination of the obtained reduced coenzyme $Q_{10}$ with various impurities, or in order to obtain a slurry with good characteristics. The crystallization rate per unit time is, for example, preferably not higher than such rate that about 50% of the whole amount of crystals to be obtained per unit time (i.e. at most 50% of the whole amount/hour) more preferably not higher than such rate that about 25% of the whole amount of crystals to be obtained per unit time (i.e. at most 25% of the whole amount/hour). The cooling rate in the cooling crystallization is generally not higher than about 40° C./hour, and preferably not higher than about 20° C./hour.

The oxidation protection effect on reduced coenzyme $Q_{10}$ in a solvent tends to be further increased in a highly concentrated reduced coenzyme $Q_{10}$ solution. Therefore, although there is no particular restriction, it would be more effective to crystallize reduced coenzyme $Q_{10}$ in a solution containing generally 1 part by weight or more, and preferably 2 parts by weight or more of reduced coenzyme $Q_{10}$ relative to 190 parts by weight of a solvent. The upper limit of the crystallization concentration cannot be absolutely specified since it may vary depending on the species of a crystallization solvent or a crystallization method. For example, however, reduced coenzyme $Q_{10}$ is contained in the amount of preferably about 15 parts by weight or less, more preferably about 13 parts by weight or less, and particularly preferably about 10 parts by weight or less relative to 100 parts by weight of a crystallization solvent at completion of crystallization. Generally, crystallization can be favorably carried out when the above amount is about 5 to 10 parts by weight.

Preferably, the thus-obtained reduced coenzyme $Q_{10}$ crystal can be recovered as a wet product, for example, by such a solid-liquid separation technique as centrifugation, pressure filtration or vacuum filtration, if necessary followed by cake washing. They can be recovered also as a dry product by further charging the wet product in a reduced pressure drier (a vacuum drier) internally purged with an inert gas and drying the same under reduced pressure. The recovery in a dry form is preferred.

As the solvent which may be used in the above crystallization method, there may be mentioned the hydrocarbons, fatty acid esters, ethers, alcohols, fatty acids, ketones, nitrogen compounds (including nitrides and amides), sulfur-containing compounds, water, etc. mentioned above. However, the most preferable solvent is, as described above, a mono- or dihydric alcohol and/or a water-soluble solvent other than alcohols. Preferred among them are methanol, ethanol, 1-propanol, 2-propanol, acetone, methyl ethyl ketone, water or a mixture thereof, and particularly preferred are ethanol, acetone or a mixture thereof.

When a mono- or dihydric alcohol or a ketone, or preferably a mono- or dihydric alcohol or a water-soluble ketone (specifically, methanol, ethanol, 1-propanol, 2-propanol, acetone, methyl ethyl ketone, etc., and preferably ethanol, acetone, etc.) is used, a reduced coenzyme $Q_{10}$ crystal having excellent slurry property and crystallinity may be obtained.

Furthermore, in view of obtaining high yield by suitably decreasing the solubility of reduced coenzyme $Q_{10}$, improving the slurry properties, and what is particularly to be noted, significantly improving solid-liquid dissolubility (filterability), it is particularly preferable that a small amount of water exists In a mono-or dihydric alcohol and/or a water-soluble organic solvent other than alcohols. The ratio of the mono- or dihydric alcohol and/or the water-soluble organic solvent other than alcohols and water cannot be absolutely specified since It may vary depending on the species of the solvent. The ratio is not particularly restricted provided that the above mono- or dihydric alcohol and/or the water-soluble organic solvent other than alcohols are substantially comprised as a main component. The lower limit of the ratio of the above mono- or dihydric alcohol and/or the water-soluble organic solvent other than alcohols relative to 100 parts by weight of the whole amount of the solvent is generally about 90 parts by weight, preferably about 91 parts by weight, more preferably about 92 parts by weight, and particularly preferably about 93 parts by weight. The upper limit of the same is generally about 99.5 parts by weight, preferably about 99 parts by weight, more preferably about 98 parts by weight, and particularly preferably about 97 parts by weight. Usually, crystallization may be carried out most preferably when the above ratio is about 93 to 97 parts by weight.

The oxidation protection effect on reduced coenzyme $Q_{10}$ in a solvent tends to be further increased in a highly concentrated reduced coenzyme $Q_{10}$ solution. Therefore, although there is no particular restriction, it would be more effective to crystallize reduced coenzyme $Q_{10}$ in a solution containing generally 1 part by weight or more, and preferably 2 parts by weight or more of reduced coenzyme $Q_{10}$ relative to 100 parts by weight of a solvent.

According to the present invention, it is possible to convert reduced coenzyme $Q_{10}$ into a crystalline state in such a condition that undesirable side reaction by oxygen is minimized by crystallization in the presence of ascorbic acid and/or citric acid or a related compound thereof, thus a reduced coenzyme $Q_{10}$ crystal of high quality may be obtained in a high yield.

The reduced coenzyme $Q_{10}$ crystal obtained by the crystallization method of the present invention is of quite high quality, and the weight ratio of reduced coenzyme $Q_{10}$/oxidized coenzyme $Q_{10}$ of 98/2 or more, and preferably 99/1 or more can be expected.

Next, the production method of reduced coenzyme $Q_{10}$ is described. In the present invention, oxidized coenzyme $Q_{10}$ is reduced to reduced coenzyme $Q_{10}$ by using ascorbic acid or a related compound thereof, then the generated reduced coenzyme $Q_{10}$ is successively crystallized in the presence of citric acid or a related compound thereof and/or ascorbic acid or a related compound thereof (direct isolation method (one-pot method) ) The term "successively crystallize" as used herein means to crystallize a reaction solution obtained by a reduction reaction without carrying out additional operations such as extraction and washing. The operation is simplified and minimized by this method, thus oxidation by a molecular oxygen can be minimized.

First, a reduction reaction is explained. In the present invention, the ascorbic acid or a related compound thereof mentioned above is used as a reducing agent.

The amount of the ascorbic acid or a related compound thereof mentioned above is not particularly restricted but may be such that favorable effects or capabilities to be expected can be exerted (i.e. effective amount). Specifically, it may be such an effective amount that oxidized coenzyme $Q_{10}$ can be converted to reduced coenzyme $Q_{10}$. Generally, the amount is 1 mole or more, and preferably 1.2 moles or more per mole of oxidized coenzyme $Q_{10}$. The upper limit of the amount is not particularly restricted, but also from an economical viewpoint, it is generally 10 moles, preferably 5 moles and more preferably 3 moles.

Citric acid or a related compound thereof may be added on the time of the reduction reaction from the viewpoint of stabilization effect in the successive crystallization, although it does not work as a reducing agent.

The reduction using ascorbic acid or a related compound thereof mentioned above may be carried out under coexistence of an additive having reaction promoting effects such as a basic substance or bisulfite as a reaction accelerator (e.g. for reaction temperature lowering, reaction time shortening, etc.) in producing reduced coenzyme $Q_{10}$.

The basic substance mentioned above is not particularly restricted, but there may be mentioned, for example, both inorganic and organic compounds. The above inorganic compound is not particularly restricted, but there may be mentioned, for example, hydroxides, carbonates and hydrogencarbonates of metals (preferably an alkaline metal, an alkaline earth metal, etc.), ammonia, etc. As the typical examples, there may be mentioned, for example, alkaline metal hydroxides such as sodium hydroxide and the like, alkaline metal carbonates such as sodium carbonate and the like, alkaline metal hydrogencarbonates such as sodium hydrogencarbonate and the like, alkaline earth, metal carbonates such as magnesium carbonate and the like, etc. The above organic compound is not particularly restricted, but there may be mentioned, for example, amines such as triethylamine. Among the above basic substances, particularly preferred are weak basic substances (weak basic or weak alkaline substances) which are inorganic compounds such as carbonates and hydrogencarbonates of metals (preferably alkaline metals, alkaline earth metals, etc.), ammonia, etc.; and organic compounds such as amines, e.g. triethylamine, and the like. Most preferred is the above-mentioned inorganic substance, and more preferred is the above-mentioned weak basic, inorganic compound.

Moreover, as the bisulfite, there may be mentioned, for example, alkaline metal bisulfites such as sodium bisulfite, end the like are preferred.

The amount of the additive mentioned above is not particularly restricted but may be such that the reaction promoting effect of the additive can be exerted to a desired extent (effective amount). From an economical viewpoint, however, the amount is generally not more than 20 moles, preferably not more than 10 moles, more preferably not more than 5 moles, and still more preferably not more than 2 moles, per mole of ascorbic acid or a related compound thereof. The lower limit of the amount is not particularly restricted but, generally, not less than 0.01 moles, preferably not less than 0.05 moles, more preferably not less than 0.1 moles, and still, more preferably not less than 0.2 moles, per mole of ascorbic acid or a related compound thereof.

A reduction reaction described in the present invention is favorably carried out under forced flowing. The stirring power consumption to provide such flowing per unit volume is generally not less than about 0.01 kW/m$^3$, preferably not lass than about 0.1 kW/m$^3$, and more preferably not less than about 0.3 kW/m$^3$. The above forced flowing is generally provided by the turning of a stirring blade(s). However, the use of a stirring blade(s) is not always necessary if the above flowing can be otherwise obtained. For example, a method based on liquid circulation may be utilized.

The reduction temperature is generally at 30° C. or higher, preferably at 40° C. or higher, more preferably at 50° C. or higher. The upper limit of the temperature is the boiling point of a system. Thus, reduction can be carried out generally at about 30 to 150° C., preferably at about 40 to 120° C., more preferably at about 50 to 100° C.

The reaction concentration is not particularly restricted but the weight of oxidized, coenzyme $Q_{10}$ relative to 100 parts by weight of a solvent is generally nor less than about 1 part by weight, preferably not less than 3 parts by weight, more preferably not less than 10 parts by weight, and still more preferably not leas than 15 parts by weight- The upper limit of the weight is not particularly restricted but is generally about 60 parts by weight, preferably 50 parts by weight, more preferably 40 parts by weight, and still more preferably 30 parts by weight. Usually, the reaction can be favorably carried out at a reaction concentration of about 2 to 30 parts by weight, preferably about 5 to 30 parts by weight, and more preferably about 10 to 30 parts by weight.

The time of reduction reaction may vary depending on the species and/or the amount of a reducing agent, hence cannot be absolutely specified. Generally, however, the reaction can be driven to completion within 48 hours, preferably within 24 hours, more preferably within 10 hours, and still more preferably within 5 hours.

After carrying out a reduction reaction by the above-mentioned method, successively, previously described crystallization is carried out from, a reaction solution. In this case, the crystallization may be carried out if the effective amount of citric acid or a related compound thereof and/or ascorbic acid or a related compound thereof described in the above crystallization method exists in a system. They may be the ascorbic acid or a related compound thereof (and the citric acid or a related, compound thereof) added in a reduction reaction. It is preferable that the ascorbic acid or a related compound, which is added in the step of reduction reaction, remains and coexists during crystallization. A preferable embodiment of the crystallization method in the method for producing reduced coenzyme $Q_{10}$ mentioned above is the same as the crystallization method already described above.

As the solvent which may be used in the above production method, there may be mentioned the hydrocarbons, fatty acid esters, ethers, alcohols, fatty acids, ketones, nitrogen compounds (including nitriles and amides), sulfur-containing compounds, water, etc. described above. However, the most preferred solvent is a mono- or dihydric alcohol and/or a water-soluble organic solvent other than alcohols as described above. Among them, particularly preferred are methanol, ethanol, 1-propanol, 2-propanol, acetone, methyl ethyl ketone, water or a mixture thereof, and most preferred are ethanol, acetone, water or a mixture thereof.

When a mono- or dihydric alcohol or ketone, preferably a mono- or dihydric alcohol or a water-soluble ketone (specifically, methanol, ethanol, 1-propanol, 2-propanol, acetone, methyl ethyl ketone, etc., and preferably, ethanol, acetone, etc.) is used, a reduced coenzyme $Q_{10}$ crystal having excellent slurry properties and crystallinity may be obtained.

Furthermore, in view of obtaining high yield by suitably decreasing solubility of reduced coenzyme $Q_{10}$, improving the slurry properties, and what is particularly to be noted, significantly improving solid-liquid dissolubility (filterability), it is particularly preferable that a smell amount of water exists in a mono- or dihydric alcohol and/or a water-soluble organic solvent other than alcohols in crystallization. The ratio of the mono- or dihydric alcohol and/or the water-soluble organic solvent other than alcohols and water cannot be absolutely specified since it may vary depending on the species of a solvent. The ratio is not particularly restricted provided that the above mono- or dihydric alcohol and/or the water-soluble organic solvent other than alcohol's are substantially comprised as a main component. The lower limit of the ratio of the above mono- or dihydric alcohol and/or the water-soluble organic solvent other than alcohols relative to 100 parts by weight of the whole amount of the solvent is generally about 90 parts by weight, preferably about 31 parts by weight, more preferably about 92 parts by weight, and particularly preferably about 93 parts by weight. The upper limit of the same is generally about 99.5 parts by weight, preferably about 99 parts by weight, more preferably about 98 parts by weight, and particularly preferably about 97 parts by weight. Usually, crystallization may be carried out most preferably when the above ration is about 93 to 97 parts by weight.

The oxidation protection effect on reduced coenzyme $Q_{10}$ in a solvent tends to be further increased in a highly concentrated reduced coenzyme $Q_{10}$ solution. Therefore, although there is no particular restriction, it would be more effective to crystallize reduced coenzyme $Q_{10}$ in a solution containing generally 1 part by weight or more, and preferably 2 parts by weight or more of reduced coenzyme $Q_{10}$ relative to 100 parts by weight of a solvent.

By the production method of the present invention, a reduced coenzyme $Q_{10}$ crystal of quite high quality, that is, in which the weight ratio of reduced coenzyme $Q_{10}$/oxidized coenzyme $Q_{10}$ is 98/2 or more, preferably 99/1 or more may be obtained in a convenient and stable manner.

The above-mentioned production method is highly effective also as a purification method from reduced coenzyme $Q_{10}$ containing oxidized coenzyme $Q_{10}$ for increasing the weight ratio of reduced coenzyme $Q_{10}$.

Next, the composition of the present invention is explained. One of the compositions of the present invention is a composition containing reduced coenzyme $Q_{10}$ which comprises reduced coenzyme $Q_{10}$ and citric acid or a related compound thereof. In the composition of the present invention, the above-mentioned hydrocarbons, fatty acid esters, ethers, alcohols, fatty acids, ketones, nitrogen compounds (including nitriles and amides), sulfur-containing compounds, water, etc. may be used as a solvent. Particularly preferred are the above-mentioned mono- or dihydric alcohol and/or a water-soluble solvent other than alcohols (preferably a water-soluble organic solvent).

And another composition of the present invention is a composition containing reduced coenzyme $Q_{10}$ which comprises reduced coenzyme $Q_{10}$, ascorbic acid or a related compound thereof, and a mono- or dihydric alcohol and/or a water-soluble solvent other than alcohols, and content of said mono- or dihydric alcohol and/or the water-soluble solvent other than alcohols being 5% by weight or more in the whole composition.

In the above-mentioned composition of the present invention, the ascorbic acid or a related compound thereof and the citric acid or a related compound thereof may foe used in combination.

The amount of the citric acid or a related compound thereof and/or the ascorbic acid or a related compound thereof to be used in the present invention may be, for example, such that favorable effects or capabilities to be expected can be exerted (i.e. effective amount). Specifically, it may be such an effective amount that oxidation of reduced coenzyme $Q_{10}$ to oxidized coenzyme Ops can be prevented. Although the amount to be used may vary depending on the species of the citric acid or a related compound thereof and/or the ascorbic acid or a related compound thereof, and is not particularly restricted, it is generally 0.1 parts by weight or more, preferably 1 part by weight or more, and more preferably 10 parts by weight or more relative to 100 parts by weight of reduced coenzymes And it may be generally 0.01 parts by weight or more, preferably 0.1 parts by weight or more relative to 100 parts by weight of a solvent. The upper limit of the amount is not particularly restricted, but also from an economical viewpoint, it may be generally 10 parts by weight or less, preferably 5 parts by weight or less, and more preferably 1 part by weight or less.

As the solvent which may be used in the composition of the present invention, there may be mentioned the hydrocarbons, fatty acid esters, ethers, alcohols, fatty acids, ketones, nitrogen compounds (including nitriles and amides), sulfur-containing compounds, water, ate. mentioned above. However, the most preferable solvent is, as described above, a mono- or dihydric alcohol and/or a water-soluble solvent other than alcohols.

For the composition of the present invention, a preferable solvent may be selected and used according to the purpose and application. For example, in view of isolating reduced coenzyme $Q_{10}$, or using the obtained reaction mixture for further derivatization (a successive reaction), a solvent having a boiling point of generally 150° C. or below, and further 100° C. or below may be particularly preferably used. In addition, when the composition is used for foods, medical purposes, etc., preferred are ethanol, 1,2-propanediol, polyethylene glycol (preferably a polyethylene glycol with a molecular weight of 300 to 1000), etc.

The amount of the mono- or dihydric alcohol and/or the water-soluble solvent other than alcohols (preferably a water-soluble organic solvent; mentioned above to be used is, for example, generally 5% by weight or more, preferably 10% by weight or more, more preferably 20% by weight or more, still more preferably 30% by weight or more, particularly preferably 40% by weight or more, more particularly preferably 50% by weight or more, and most preferably more than 50% by weight, in the whole composition. In particular, when the ascorbic acid or a related compound thereof is used, the amount of the solvent mentioned above to be used Is preferably 60% by weight or more, more preferably 70% by weight or more, and still more preferably 80% by weight or more. When the composition of the present invention is used for foods, medical purposes, or preferably for foods or medical oral administration, very preferable lower limit of the solvent is generally 5% by weight, preferably 10% by weight, more preferably 20% by weight, still more preferably 30% by weight, particularly preferably 40% by weight, and most preferably 50% by weight in the whole composition. At the same time, very preferable upper limit of the same is, generally 99% by weight, preferably 95% by weight, more preferably 90% by weight, still more preferably 85% by weight, particularly preferably 80% by weight, and most preferably 70% by weight in the whole composition.

Reduced coenzyme $Q_{10}$ may be provided in the form of either the above reaction mixture obtained by the production method of the present invention, or a mixture obtainable by externally adding reduced coenzyme $Q_{10}$. For the external addition, one isolated from the above reaction mixture or one separately synthesized and isolated may be used, for example.

When a reaction mixture is used, while there is an advantage that it is convenient, there is also a concern for a possibility that byproducts or the like, generated in a reduction reaction, which are not always, physically preferable, may coexist in a composition. In this viewpoint, it is preferable to use reduced coenzyme $Q_{10}$ in the form of a mixture obtainable by externally adding it. than the above reaction mixture.

additionally, needless to say, the composition of the present invention does not inhibit coexistence of another active substance other than reduced coenzyme $Q_{10}$. As the another active substance, there may be mentioned, for example, amino acids, vitamins, minerals, polyphenols, organic acids, sugars, peptides, proteins, etc.

Although the composition of the present, invention may be used as it is, if may preferably be used in oral administration forms such as a capsule (a hard capsule, a soft capsule), a tablet, syrup and a drink by a further process. Moreover, forms such as cream, a suppository, toothpaste, etc. may also be applicable by a further process. Particularly preferred is a capsule, and most preferred is a soft capsule. A capsule material is not particularly restricted, and typically includes gelatin derived from, a beef bone, oxhide, a pig skin, a fish skin, etc., and also includes other materials (e.g. thickening stabilizers for example seaweed-derived products such as carrageenan, alginic acid and the like, vegetable seed-derived products such as locust bean gum and guar gum, etc., which are usable as food additives, and agents for manufacturing including celluloses).

By carrying out the stabilization method, preservation method, crystallization method and production method of reduced coenzyme $Q_{10}$ according to the present invention under a deoxidized atmosphere, the oxidation protection effect may be improved. Additionally, it is preferable to prepare or preserve the composition of the present invention under a deoxidized atmosphere. The deoxidized atmosphere can be attained by substitution with an inert gas, pressure reduction, boiling, or a combination of these. It is preferable to carry out at least the substitution with an inert gas, namely to use an inert gas atmosphere. As the inert gas, there may be mentioned, for example, nitrogen gas, helium gas, argon gas, hydrogen gas, carbon dioxide gas and the like. Nitrogen gas is preferred, however.

In the stabilization method and the composition mentioned above, it is expectable to maintain the weight ratio of reduced coenzyme $Q_{10}$ (reduced coenzyme $Q_{10}$+oxidized coenzyme $Q_{10}$) of 90% by weight or more, and preferably 95% by weight or more, after a given period, of preservation. The above preservation period is, for example, 1 day or more, preferably 1 week or more, more preferably 1 month or more, still more preferably half a year Or more, particularly preferably 1 year or more, and most preferably 2 years or more.

In the present invention, an agent which is safe and easy to handle are used, and a solvent to be used may be suitably selected according to the purpose and application. Furthermore, the present invention is suitably used for isolation or further derivatization of reduced coenzyme $Q_{10}$, and for compositions and oral administration forms such as for foods, medical purpose and the like. Therefore, the present invention can be utilized for many applications and thus has a great advantage.

BEST MODE FOR CARRYING OUT THE INVENTION

The following examples illustrate the present invention in further detail. These examples are, however, by no means limitative of the scope of the present invention.

In the examples, purity of reduced coenzyme $Q_{10}$ and the weight ratio of reduced coenzyme $Q_{10}$/oxidized coenzyme $Q_{10}$ were determined by the HFLC analysis specified below. The reduced coenzyme $Q_{10}$ purity values as determined, however, are by no means indicative of the limit purity value attainable in accordance with the present invention. Likewise, the ratio of the reduced coenzyme $Q_{10}$ in the weight ratio of reduced coenzyme $Q_{10}$/oxidized coenzyme $Q_{10}$ values obtained never indicates the upper limit to that ratio. (HPLC Conditions)

Column; SYMMETRY C18 (product of Waters), 250 mm (in length), 4.6 mm (in inside diameter): mobile phase; $C_2H_5OH/CH_3OH=4/3$ (v/v); detection wavelength; 210 nm; flow rate; 1 ml/min: retention time of reduced coenzyme $Q_{10}$; 9.1 min: retention time of oxidized coenzyme $Q_{10}$; 13.3 min.

Example 1

To 1000 g of ethanol, oxidized coenzyme $Q_{10}$ (100 g; containing 0.40% of oxidized coenzyme $Q_9$, purity 33,4%) and 60 g of L-ascorbic acid were added, and the mixture was stirred at 78° C. to carry out a reduction reaction. After the lapse of 30 hours, the mixture was cooled to 50° C. and was added with 400 g of ethanol while maintaining the same temperature. This ethanol solution (containing 100 g of reduced coenzyme $Q_{10}$ (containing 0.40% of reduced coenzyme $Q_9$)) was cooled to 2° C. at a cooling rate of 10° C./hour while stirring (stirring power consumption: 0.3 kW/m$^3$) to give a white slurry. The slurry obtained was filtered under reduced pressure, and the wet crystal was washed in sequence with cold ethanol, cold water and cold ethanol (the temperature of cold solvents used for washing: 2° C.). The wet crystal was further dried under reduced pressure (20 to 40° C. 1 to 30 mmHg) to give 95 g of a white dry crystal (containing 0.21% of reduced coenzyme $Q_9$: removal percentage; 48%) (isolated product yield; 95 moles %). All the operations except for reduced-pressure drying were carried out in a nitrogen atmosphere. The weight ratio of reduced coenzyme $Q_{10}$/oxidized coenzyme $Q_{10}$ of the crystal obtained was 99.5/0.5, and the purity of the reduced coenzyme Q10 was 99.2%.

Example 2

Oxidized coenzyme $Q_{10}$ (100 g) was dissolved in 1000 g of heptane at 25° C. while stirring the above oxidized coenzyme $Q_{10}$-heptane solution (stirring power consumption: 0.3 kW/m$^3$), an aqueous solution prepared by dissolving 100 g of sodium dithionite (purity: at least 75%), as a reducing agent. In 1000 ml of water was gradually added to the above heptane solution, and a reduction reaction was carried out at 25° C. and at pH between 4 and 6. After the lapse of 2 hours, an aqueous phase was removed from the reaction, mixture, and the heptane phase was washed for 6 times with 1000 g of deaerated saturated brine. All the above operations were carried out in a nitrogen atmosphere. This heptane solution was subjected to solvent substitution under reduced pressure to prepare an ethanol solution comprising 1 part by weight of reduced coenzyme $Q_{10}$ relative to 100 parts by weight of ethanol.

This ethanol solution was dispensed, and the ascorbic acid or the citric acid or a related compound thereof shown in Table 1 was separately added so that it is contained in 0.1 parts by weight relative to 100 parts by weight of ethanol (10 parts by weight relative to 100 parts by weight of reduced coenzyme $Q_{10}$). Then, the solutions were stirred in air at 23° C. The weight ratios of reduced coenzyme ($Q_{10}$/oxidized coenzyme $Q_{10}$ after the lapse of 24 hours are shown in Table 1. For comparison, a result in the case of additive-free is also shown.

TABLE 1

| Additive | R |
| --- | --- |
| L-ascorbic acid | 95.3/4.7 |
| L-ascorbyl stearate | 95.8/4.2 |
| L-ascorbyl palmitate | 95.4/4.6 |
| Citric acid | 96.3/3.7 |
| Isopropyl Citrate | 95.9/4.1 |
| Additive-free | 56.0/44.0 |

R: The weight ratio of reduced coenzyme$Q_{10}$/oxidized coenzyme $Q_{10}$

Reference Example 1

An ethanol solution was prepared by the same procedure as in Example 2. The antioxidants shown in Table 2 were added in 0.1 parts by weight relative to 100 parts by weight of ethanol (10 parts by weight relative to 100 parts by weight of reduced coenzyme $Q_{10}$), and the solutions were stirred in air at 25° C., The weight ratios of reduced coenzyme $Q_{10}$/oxidized coenzyme $Q_{10}$ after the lapse of 24 hours are shown in Table 2.

TABLE 2

| Additive | R |
|---|---|
| n-propyl gallate | 4.5/95.5 |
| Vitamin E | 44.2/55.8 |
| Qurcetin | 3.5/96.5 |
| Rutin | 16.1/83.9 |
| γ-Oryzanol | 55.3/44.7 |
| Butylhydroxytoluene | 51.1/48.9 |
| Butylhydroxyanisol | 56.0/44.0 |

R: The weight ratio of reduced coenzyme$Q_{10}$/oxidized coenzyme $Q_{10}$

Example 3

Using the reduced coenzyme $Q_{10}$ crystal obtained in Example 1, an ethanol solution containing 5 parts by weight of reduced coenzyme $Q_{10}$ relative to 100 parts by weight of ethanol was prepared. To this ethanol solution, L-ascorbic acid was added so that 1 part by weight of L-ascorbic acid was contained relative to 100 parts by weight of the solvent (20 parts by weight relative to 100 parts by weight of reduced coenzyme $Q_{10}$), and the solution was stirred in air at 50° C. The weight ratio of reduced coenzyme $Q_{10}$/oxidized coenzyme $Q_{10}$ after the lapse of 50 hours, and residual ratios of L-ascorbic acid are shown in Table 3, For comparison, results in the cases of each of reduced coenzyme $Q_{10}$ and L-ascorbic acid being respectively used singly are also shown. From these results, it was suggested that stabilization effect on reduced coenzyme $Q_{10}$ by existence of L-ascorbic acid was not based on the reduction reaction of oxidized coenzyme $Q_{10}$ generated by air oxidation, with L-ascorbic acid.

TABLE 3

|  | R | X |
|---|---|---|
| Reduced coenzyme$Q_{10}$ + L-ascorbic acid | 99.5/0.5 | 87.7% |
| Reduced coenzyme $Q_{10}$ | 74.1/25.9 | — |
| L-ascorbic acid | — | 85.2% |

R: The weight ratio or reduced coenzyme$Q_{10}$/oxidized coenzyme $Q_{10}$
X: The residual ratio of ascorbic acid Example 4

To 100 parts by weight of ethanol, 1 part by weight of the reduced coenzyme $Q_{10}$ crystal obtained in Example 1, and 1 part by weight of ascorbic, acid or a related compound thereof shown in Table 4 were added, and the mixture was stirred at 45° C. in air. The weight ratios of reduced coenzyme $Q_{10}$/oxidized coenzyme $Q_{10}$ after the lapse of 24 hours are shown in Table 4. For comparison, a result in the case of additive-free is also shown.

TABLE 4

| Additive | R |
|---|---|
| L-ascorbic acid | 99.1/0.9 |
| L-ascorbyl palmitate | 98.8/1.2 |
| Additive-free | 12.3/87.7 |

R: The weight ratio of reduced coenzyme$Q_{10}$/oxidized coenzyme $Q_{10}$

Comparative Example 1

To 100 parts by weight of glycerin, 1 part by weight of the reduced coenzyme $Q_{10}$ crystal obtained in Example 1, and 1 part by weight of ascorbic acid or a related compound thereof shown in Table 5 were added, and the mixture was stirred at 45° C. in air. The weight ratios of reduced coenzyme $Q_{10}$/oxidized coenzyme $Q_{10}$ after the lapse of 24 hours are shown in Table 5. For comparison, a result in the case of additive-free is also shown.

TABLE 5

| Additive | R |
|---|---|
| L-ascorbic acid | 89.2/10.8 |
| L-ascorbyl palmitate | 86.0/14.0 |
| Additive-free | 83.4/16.6 |

R: the weight ratio of reduced coenzyme$Q_{10}$/oxidized coenzyme $Q_{10}$

Example 5

To 1000 g of ethanol, oxidized coenzyme $Q_{10}$ (100 g; containing 0.40% of oxidized coenzyme $Q_9$, purity 99.4%) and 60 g of L-ascorbic acid were added, and the mixture was stirred at 78° C. to carry out a reduction reaction. After the lapse of 30 hours, the mixture was cooled to 50° C., and added with 330 g of ethanol and 70 g of water while maintaining the same temperature. This ethanol solution (containing 100 g of reduced coenzyme $Q_{10}$ (containing 0.40% of reduced coenzyme $Q_9$) was cooled to 2° C. at a cooling rate of 10° C./hour while stirring (stirring power consumption: 0.3 kW/m$^3$) to give a white slurry. The slurry showed very good fluidity as compared with the one in Example 1, and was easily brushed away from a crystallization container. The slurry obtained was filtered under reduced pressure, and the wet crystal was washed in sequence with cold ethanol, cold water and cold ethanol (the temperature of cold solvents used for washing: 2° C). The wet crystal was further dried under reduced pressure (20 to 40° C., 1 to 30 mmHg) to give 97 g of a white dry crystal (containing 0.24% of reduced coenzyme $Q_9$: removal percentage; 41%) (isolated product yield: 97 mole %). All the operations except for reduced-pressure drying were carried out in a nitrogen atmosphere. The weight ratio of reduced coenzyme $Q_{10}$/oxidized coenzyme $Q_{10}$ of the crystal obtained was 99.5/0.5, and the purity of the reduced coenzyme $Q_{10}$ was 99.2%.

Example 6

To 1000 g of ethane-X, oxidized coenzyme $Q_{10}$ (100 g; purity 99.4%), 60 g of L-ascorbic acid and 30 g of sodium hydrogencarbonate were added, and the mixture was stirred at 78° C. to carry out a reduction reaction. After the lapse of 30 hours, the mixture was cooled to 50° C., and was added with 330 g of ethanol and 70 g of water while maintaining the same temperature. This ethanol solution was cooled to 2° C. at a cooling rate of 10° C./hour while stirring (stirring power consumption: 0-3 kW/m$^3$) to give a white slurry. The slurry showed very good fluidity as compared with the one in Example 1, and was easily brushed away from a crystallization container. The slurry obtained was filtered under reduced pressure, and the wet crystal was washed in sequence with cold ethanol, cold water and cold ethanol (the temperature of cold solvents used for washing: 2° C.). The wet crystal was further dried under reduced pressure (20 to 40° C., 1 to 30 mmHg) to give 97 g of a white dry crystal (isolated product yield: 97 mole %). All the operations except for reduced-pressure drying were carried out in a nitrogen atmosphere. The weight ratio of reduced coenzyme $Q_{10}$/oxidized coenzyme $Q_{10}$ of the crystal obtained was 99.5/0.5, and the purity of the reduced coenzyme $Q_{10}$ was 99.2%.

Example 7

To 1000 g of acetone, oxidized coenzyme $Q_{10}$ (100 g; containing 0.40% of oxidized coenzyme $Q_9$, purity 99.4%), 60 g of L-ascorbic acid and 30 g of sodium hydrogencarbonate were added, and the mixture was stirred at 50° C. to carry out a reduction reaction. After the lapse of 45 hours, the mixture was added with 400 g of acetone while maintaining the same temperature. This acetone solution (containing 100 g of reduced coenzyme $Q_{10}$ (containing 0.40% of reduced coenzyme $Q_9$) was cooled to 2° C. at a cooling rate of 10° C./hour while stirring (stirring power consumption: 0.3 kW/m$^3$) to give a white slurry. The slurry obtained was filtered under reduced pressure, and the wet crystal was washed in sequence with cold acetone, cold water and cold acetone (the temperature of cold solvents used for washing: 2° C.). The wet crystal was further dried under reduced pressure (20 to 40° C., 1 to 30 mmHg) to give 93 g of a white dry crystal (containing 0.23% of reduced coenzyme $Q_9$: removal percentage; 42%) (isolated product yield; 93 mole %). All the operations except for reduced-pressure drying were carried out in a nitrogen atmosphere. The weight ratio of reduced coenzyme $Q_{10}$/oxidized coenzyme $Q_{10}$ of the crystal obtained was 99.6/0.4, and the purity of the reduced coenzyme $Q_{10}$ was 99.3%.

Example 8

A reduction reaction, and an addition of ethanol and water were carried out under exactly the same conditions as in Example 5 except that oxidized coenzyme $Q_{10}$ used had purity of 98.4% (containing 1.0% of oxidized coenzyme $Q_9$, 0.30% of oxidized coenzyme $Q_8$ and 0.04% of oxidized coenzyme $Q_7$. Thereby, a hydroethanolic solution of reduced coenzyme $Q_{10}$ at 50° C. was prepared (containing 1.00% of reduced coenzyme $Q_9$, 0.30% of reduced coenzyme $Q_8$, and 0.40% of reduced coenzyme $Q_7$). This hydroethanolic solution was cooled to 2° C. at a cooling rate of 3° C./hour while stirring (stirring power consumption: 0.3 kW/m$^3$) to precipitate a crystal. The slurry showed very good fluidity as compared with the one in Example 1, and was easily brushed away from a crystallization container. All the operations were carried out in a nitrogen atmosphere. The slurry obtained was filtered under reduced pressure, and the wet crystal was washed in sequence with cold ethanol, cold water and cold ethanol (the temperature of cold solvents used for washing: 2° C). The wet crystal was further dried under reduced pressure (20 to 40° C., 1 to 30 mmHg) to give 95 g of a white dry crystal (containing 0.32% of reduced coenzyme $Q_9$: removal percentage; 48%: no reduced coenzyme $Q_8$ and reduced coenzyme $Q_7$ was detected) (isolated product yield: 97 mole %). The weight ratio of reduced coenzyme $Q_{10}$/oxidized coenzyme $Q_{10}$ of the crystal obtained was 99.5/0.5, and the purity of the reduced coenzyme $Q_{10}$ was 98.9%.

Example 9

Oxidized coenzyme $Q_{10}$ (100 g; purity 99.4%) was dissolved in 1000 g of heptane at 25° C. While stirring the above oxidized coenzyme $Q_{10}$-heptane solution (stirring power consumption: 0.3 kW/m$^3$), an aqueous solution prepared by dissolving 100 g of sodium dithionite (purity: at least 75%), as a reducing agent, in 1000 ml of water was gradually added to the above heptane solution and a reduction reaction was carried out at 25° C. and at pH between 4 and 6. After the lapse of 2 hours, an aqueous phase was removed from the reaction mixture, and the heptane phase was washed for 6 times with 1000 g of deaerated saturated brine. All the above operations were carried out in a nitrogen atmosphere. This heptane phase was subjected to solvent substitution under reduced pressure to obtain an ethanol solution at 50° C. containing 7 parts by weight of reduced coenzyme $Q_{10}$ relative to 100 parts by weight of ethanol. To this ethanol solution, 10 g of isopropyl citrate was added (0.7 parts by weight relative to 100 parts by weight of ethanol, and 10 parts by weight relative to 100 parts by weight of reduced coenzyme $Q_{10}$). The mixture was cooled to 2° C. by stirring in air (stirring power consumption: 0.3 kW/m$^3$) to give a white slurry. The slurry obtained was filtered under reduced pressure, and the wet crystal was washed in sequence with cold ethanol, cold water and cold, ethanol (the temperature of cold solvents used for washing: 2° C.). The wet crystal was further dried under reduced pressure (20 to 40° C., 1 to 30 mmHg) to give 95 g of a white dry crystal (isolated product yield: 95 moles). The weight ratio of reduced coenzyme $Q_{10}$/oxidized coenzyme Q10 of the crystal obtained was 99.4/0.6, and the purity of the reduced coenzyme $Q_{10}$ was 99.1%.

Example 10

By the same procedure as in Example 9, a heptane solution of reduced coenzyme $Q_{10}$ (purity 99.4%) was obtained. This heptane solution was subjected to solvent substitution under reduced pressure to obtain an ethanol solution at 50° C. containing parts by weight of reduced coenzyme $Q_{10}$ relative to 100 parts by weight of ethanol. To this ethanol solution, 10 g of L-ascorbyl stearate (0.7 parts by weight relative to 100 parts by weight of ethanol, and 10 parts by weight relative to 10.0 parts by weight of reduced coenzyme $Q_{10}$) was added. The mixture was cooled to 2° C. by stirring in air (stirring power consumption: 0.3 kW/m$^3$) to give a white slurry. The slurry obtained was filtered under reduced pressure, and the obtained wet crystal was washed in sequence with cold ethanol, cold water and cold ethanol (the temperature of cold solvents used for washing: 2° C.). The wet crystal was further dried under reduced pressure (20 to 40° C., 1 to 30 mmHg) to give 95 g of a white dry crystal, (isolated product yield: 95 mole %). The weight ratio of reduced coenzyme $Q_{10}$/oxidized coenzyme $Q_{10}$ of the crystal obtained was 99.4/0.6, and the purity of the reduced coenzyme $Q_{10}$ was 99.1%.

Example 11

A white dry crystal (95 g) was obtained by the same procedures as in Example 10 except that 1 g of L-ascorbyl stearate (0.07 parts by weight relative to 100 parts by weight of ethanol, and 1 part by weight relative to 100 parts by weight of reduced coenzyme $Q_{10}$) was added in crystallization (isolated product yield; 95 mole %). The weight ratio of reduced coenzyme $Q_{10}$/oxidized coenzyme $Q_{10}$ of the crystal obtained was 98.5/1.5, and the purity of the reduced coenzyme $Q_{10}$ was 98.2%.

Comparative Example 2

A white dry crystal (95 g) was obtained by the same procedures as in Example 10 except that L-ascorbyl stearate was not added in crystallization (isolated product yield: 95 mole %). The weight ratio of reduced coenzyme $Q_{10}$/oxidized coenzyme $Q_{10}$ of the crystal obtained was 36.4/3.5, and the purity of the reduced coenzyme $Q_{10}$ was 96.1%.

Example 12

Reduced coenzyme $Q_{10}$ crystal (2 g) obtained in Example 9 was ground with 0.2 g of ascorbic acid or citric acid, or a related compound thereof in a mortar and mixed. The weight ratios of reduced coenzyme $Q_{10}$/oxidized coenzyme $Q_{10}$ after being allowed to stand for four days at 25° C. in air are shown in Table 2. For comparison, a result in the case of additive-free is also and shown.

TABLE 6

| Additive | R |
|---|---|
| L-ascorbic acid | 86.4/13.6 |
| L-ascorbyl stearate | 85.9/14.1 |
| L-ascorbyl palmitate | 87.1/12.9 |
| Citric acid | 86.8/13.2 |
| Additive-free | 79.1/20.9 |

R: The weight ratio of reduced coenzyme$Q_{10}$/oxidized coenzyme $Q_{10}$

Example 13

Polyethylene glycol was heated to 50° C., and added with the reduced coenzyme $Q_{10}$ crystal obtained in Example 1 and L-ascorbic acid at the same temperature. Then, by a conventional method, a gelatin soft capsule formulation composed of the following components was obtained.

| | |
|---|---|
| Reduced coenzyme $Q_{10}$ | 60 parts by weight |
| L-ascorbic acid | 100 parts by weight |
| Polyethylene glycol | 1000 parts by weight |

Example 14

Polyethylene glycol was heated to 50° C., and added with the reduced coenzyme $Q_{10}$ crystal obtained in Example 1, L-ascorbic acid and ethanol at the same temperature. Then, by a conventional method, a carrageenan soft capsule formulation composed of the following components was obtained.

| | |
|---|---|
| Reduced coenzyme $Q_{10}$ | 30 parts by weight |
| L-ascorbic acid | 1 part by weight |
| Polyethylene glycol | 950 parts by weight |
| Ethanol | 50 parts by weight |

Example 15

Polyethylene glycol was heated to 50° C., and added with the reduced coenzyme $Q_{10}$ crystal obtained in Example 1 and citric acid at the same temperature. Then, by a conventional method, a gelatin soft capsule formulation composed of the following components was obtained.

| | |
|---|---|
| Reduced coenzyme $Q_{10}$ | 60 parts by weight |
| Citric acid | 10 parts by weight |
| Polyethylene glycol | 1000 parts by weight |

INDUSTRIAL APPLICABILITY

The present invention, which has the constitution described above, may provide a convenient and preferable stabilization method ox reduced coenzyme $Q_{10}$, and a preservation method, an isolation (crystallization) method and a composition of reduced coenzyme $Q_{10}$ using said stabilization method. Moreover, the invention may also provide a versatile production method of reduced coenzyme $Q_{10}$ using the above stabilization method. By the present invention, it becomes possible to stabilize, and further stably preserve reduced coenzyme $Q_{10}$. Furthermore, it also becomes possible to obtain reduced coenzyme $Q_{10}$ of high quality in a convenient and efficient manner by the method suitable for a commercial scale production.

What is claimed is:

1. A method of stabilizing reduced coenzyme Q10 which comprises subjecting reduced coenzyme Q10 to be mixed with citric acid or a related compound thereof, wherein the citric acid or related compound thereof is at least one species selected from the group consisting of citric acid, an ester thereof and a salt thereof, and in which the citric acid or the related compound thereof exists in an amount of 0.1 parts by weight or more relative to 100 parts by weight of reduced coenzyme Q10.

2. The method according to claim 1, wherein the citric acid or the related compound thereof exists as a solid phase in a liquid phase containing reduced coenzyme $Q_{10}$.

3. The method according to claim 1, wherein reduced coenzyme $Q_{10}$ exists as a solid phase in a liquid phase containing the citric acid or the related compound thereof.

4. The method according to claim 1, wherein reduced coenzyme $Q_{10}$ and the citric acid or the related compound thereof are both in the form of liquid phase or both exist in a liquid phase.

5. The method according to claim 3, wherein the liquid phase is a homogeneous phase.

6. The method according to claim 3, wherein a solvent in the liquid phase is at least one species selected from the group consisting of hydrocarbons, fatty acid esters, ethers, alcohols, fatty acids, ketones, nitrogen compounds, sulfur-containing compounds and water.

7. The method according to claim 3, wherein the solvent in the liquid phase is a mono-or dihydric alcohol and/or a water-soluble solvent other than alcohols.

8. The method according to claim 3, wherein the solvent in the liquid phase is ethanol, 1,2-propanediol or polyethylene glycol.

9. The method according to claim 1, wherein an ascorbic acid or a related compound thereof exists together with the citric acid or the related compound thereof; wherein the ascorbic acid or the related compound thereof is at least one species selected from the group consisting of ascorbic acid, rhamno-ascorbic acid, arabo-ascorbic acid, gluco-ascorbic acid, fuco-ascorbic acid, glucohepto-ascorbic acid, xylo-ascorbic acid, galacto-ascorbic acid, gulo-ascorbic acid, allo-ascorbic acid, erythro-ascorbic acid, 6-desoxyascorbic acid, and ester thereof and salt thereof.

10. A method of preserving reduced coenzyme $Q_{10}$ which comprises preserving reduced coenzyme $Q_{10}$ stabilized by the method according to claim 1 in a preservation condition of 50° C. or below.

11. The method according to claim 10, wherein reduced coenzyme $Q_{10}$ is preserved under a deoxidized atmosphere.

12. A composition containing reduced coenzyme Q10 which comprises a mixture of reduced coenzyme Q10 and citric acid or a related compound thereof, wherein the citric acid or related compound thereof is at least one species selected from the group consisting of citric acid, an ester thereof and a salt thereof, and in which 0.1 parts by weight or more of the citric acid or the related compound thereof is mixed relative to 100 parts by weight of reduced coenzyme Q10.

13. The composition according to claim 12, wherein at least one species selected from the group consisting of ethanol, 1,2-propanediol and polyethylene glycol is further contained as a solvent.

14. The composition according to claim 12, wherein ascorbic acid or a related compound thereof is further mixed together with the citric acid or the related compound thereof; wherein the ascorbic acid or the related compound thereof is at least one species selected from the group consisting of ascorbic acid, rhamno-ascorbic acid, arabo-ascorbic acid, gluco-ascorbic acid, fuco-ascorbic acid, glucohepto-ascorbic acid, xylo-ascorbic acid, galacto-ascorbic acid, gulo-ascorbic acid, allo-ascorbic acid, erythro-ascorbic acid, 6-desoxyascorbic acid, an ester thereof and salt thereof.

15. The composition according to claim 12, wherein reduced coenzyme $Q_{10}$ is externally added.

16. The composition according to claim 12, which further comprises adding another active substance other than reduced coenzyme Q10 to the mixture.

17. The composition according to claim 12, which is processed into an oral administration form.

18. The composition according to claim 17, wherein the form is a capsule.

19. The composition according to claim 18, wherein the capsule is a soft capsule.

20. The composition according to claim 12, which is prepared or preserved under a deoxidized atmosphere.

21. The method according to claim 1, wherein no vegetable oils and/or surfactants are substantially contained.

22. The composition according to claim 12, wherein no vegetable oils and/or surfactants are substantially contained.

* * * * *